United States Patent
Hammer et al.

(10) Patent No.: US 7,177,025 B2
(45) Date of Patent: Feb. 13, 2007

(54) MEASURING SPECULAR REFLECTANCE OF A SAMPLE

(75) Inventors: Michael R. Hammer, Sassafras (AU); Robert J. Francis, Glen Waverley (AU)

(73) Assignee: Varian Australia Pty Ltd, Mulgrave (AU)

( * ) Notice: Subject to any disclaimer, the term of this patent is extended or adjusted under 35 U.S.C. 154(b) by 428 days.

(21) Appl. No.: 10/472,296

(22) PCT Filed: Mar. 28, 2002

(86) PCT No.: PCT/AU02/00385

§ 371 (c)(1),
(2), (4) Date: Feb. 25, 2004

(87) PCT Pub. No.: WO02/082062

PCT Pub. Date: Oct. 17, 2002

(65) Prior Publication Data

US 2004/0136005 A1    Jul. 15, 2004

(30) Foreign Application Priority Data

Apr. 4, 2001    (AU) ..................... PR4202

(51) Int. Cl.
*G01N 21/55* (2006.01)
(52) U.S. Cl. ............... 356/445; 356/239.7; 250/227.23
(58) Field of Classification Search ........ 356/445–448, 356/239.1, 239.7, 239.8, 71–73; 250/559.16, 250/559.18, 227.2, 227.23, 227.24, 458.1, 250/459.1, 562
See application file for complete search history.

(56) References Cited

U.S. PATENT DOCUMENTS

| | | | | | |
|---|---|---|---|---|---|
| 4,171,159 | A | * | 10/1979 | White | 356/502 |
| 4,344,709 | A | * | 8/1982 | Provder et al. | 356/445 |
| 4,710,642 | A | * | 12/1987 | McNeil | 250/559.04 |
| 5,164,790 | A | * | 11/1992 | McNeil et al. | 356/496 |
| 5,403,433 | A | * | 4/1995 | Morrison et al. | 216/60 |
| 5,867,276 | A | * | 2/1999 | McNeil et al. | 356/445 |
| 5,889,593 | A | * | 3/1999 | Bareket | 356/445 |
| 6,396,579 | B1 | * | 5/2002 | Hayamizu et al. | 356/239.7 |
| 6,842,251 | B1 | * | 1/2005 | Holden | 356/445 |
| 6,980,296 | B2 | * | 12/2005 | Kwan et al. | 356/432 |

\* cited by examiner

*Primary Examiner*—Sang H. Nguyen
(74) *Attorney, Agent, or Firm*—Bella Fishman; Edward B. Berkowitz

(57) ABSTRACT

Apparatus (10) for measuring absolute specular reflectance of a surface of a sample (22) includes a sample holder (12), a light source (18) for transmitting an incident light beam (16) onto a surface of the sample (22) and a detector (26) for detecting a specularly reflected component of the incident light. The light source (18), sample holder (12) and detector (26) are mounted and operatively associate (14, 24, 28) to be relatively moveable to vary the angle of incidence of light (16) onto sample (22) and to correspondingly automatically vary the relative position of the detector (26) such that the angle of reflection equals the angle of incidence. In the absence of the sample (22) or upon removal of the sample holder (12), light (16) impinges directly onto detector (26) to directly allow measurement of the absolute intensity of the light beam (16) as a reference measurement. This avoids the need to use intervening optical components such as mirrors which may degrade over time. It also allows provision of a relatively simplified apparatus.

18 Claims, 3 Drawing Sheets

MEASURING SPECULAR REFLECTANCE OF A SAMPLE

TECHNICAL FIELD

The present invention relates to apparatus for measuring specular reflectance of a sample.

BACKGROUND

A common requirement in ultraviolet-visible spectroscopy is the ability to measure the specular (mirror-like) reflectance of a sample. One approach to making such a measurement is to arrange the path of a light beam between a light source and an optical detector so that there is a reflection off a mirrored surface. With the mirror in place the intensity received by the detector is noted. The mirror is then replaced with the sample and the intensity received by the detector is noted again. The change in intensity is a measure of the difference in reflectivity between the mirror and the sample. This approach has the disadvantage that it is necessary to know the reflectivity of the mirror before the reflectivity of the sample can be calculated. It is preferable that the result obtained be a direct measure of the reflectivity of the sample, not of its reflectivity relative to that of some other object. Such a direct measure is termed an absolute reflectance measurement as distinct from a relative reflectance measurement.

In known spectrometers the light source and the light detector are both fixed in position. The specular reflectance apparatus diverts the light beam onto the sample of interest and re-orients the reflected light back onto the detector. This requires a number of mirrors that both re-direct the beam and also re-focus it to allow for the change in path length between source and detector. Known approaches typically involve both fixed and re-positionable mirrors. The need for a plurality of mirrors makes such apparatus complex, and it is also undesirable because the mirrors deteriorate with handling and exposure to the atmosphere, progressively degrading the performance of the apparatus.

There is often a requirement not just to measure the absolute specular reflectance of a sample, but also to measure its absolute specular reflectance as a function of the incidence angle of the light beam. This additional requirement can add considerable complexity to conventional approaches, making implementation difficult.

The discussion of the background to the invention hereinabove is included to explain the context of the invention. This is not to be taken as an admission that any of the material referred to was published, known or part of the common general knowledge in Australia as at the priority date of the present application.

An object of the present invention is to provide relatively simple apparatus whereby the absolute specular reflectance of a sample as a function of incident angle of the light can be determined directly.

DISCLOSURE OF THE INVENTION

According to a first aspect of the present invention there is provided apparatus for measuring specular reflectance of a sample including a sample holder, a light source for transmitting a beam of light at a predetermined angle of incidence onto a surface of a sample when held by the sample holder, the light source and the sample holder being mounted for relative movement to vary said angle of incidence, and a detector for detecting light of said beam which is specularly reflected from said surface of the sample, the detector and the sample holder also being mounted for relative movement, wherein the light source, the detector and the sample holder are correspondingly relatively positionable for a specularly reflected component of a transmitted light beam to be detected for different angles of incidence of the light beam.

According to a second aspect, the present invention is realisable as an accessory for use in a spectrometer wherein the light source is a component of the spectrometer and not the accessory. Thus the invention also provides accessory apparatus for a spectrometer for measuring specular reflectance of a sample including a sample holder which is positionable relative to a light source of the spectrometer for the light source to transmit a beam of light at a predetermined angle of incidence onto a surface of a sample when held by the sample holder, the sample holder being mounted for movement relative to the light source to vary said angle of incidence, and a detector for detecting light of said beam which is specularly reflected from said surface of the sample, the detector being mounted for movement relative to the sample holder, wherein the detector and the sample holder are correspondingly relatively positionable for a specularly reflected component of a transmitted light beam to be detected for different angles of incidence of the light beam.

Preferably the sample holder is structured, and the light source and detector are positionable relative to the sample holder and each other, such that in the absence of a sample in the sample holder, the light source and detector can be so positioned that a light beam transmitted from the light source will directly impinge on the detector. Alternatively the sample holder may be removable and the light source and detector relatively positionable to achieve the same result. Thus the detector can directly measure the absolute intensity of the light beam as a reference measurement.

Preferably the sample holder, light source and detector are also mounted such that the respective distances therebetween remain constant for different positionings of the sample holder, light source and detector; that is, such that the path length from the light source to the detector remains constant for reference and sample measurements at any angle. Consequently, there is no change in optical focus point between reference and sample measurements. This eliminates the need for any optical re-imaging. Thus the apparatus of this invention requires no mirrors and for this reason it is much more immune to degradation through handling and use compared to prior art apparatus. It is also advantageous if the path length from light source to sample, and the path length from sample to detector, each remain separately constant. This ensures the normal projection of the illuminated patch size on the sample does not change as the angle of incidence is varied.

The apparatus may be such that any one of the light source, sample holder or detector may be fixed in position and the other two components movable relative thereto. Thus, for example, the light source may be fixed in position (as will be the case for the accessory apparatus of the second aspect of the invention) and the sample holder and detector movable. Preferably the movable components are operatively associated such that movement of one correspondingly automatically moves the other to a correct position.

For example, for a movable sample holder and detector, the sample holder may be rotatable about a central axis passing through the holder and perpendicular to the incident light beam such that a surface of a held sample may be aligned at different angles to the direction of a light beam from the fixed light source, and the detector mounting operatively associated with the sample holder rotating about the same central axis as the sample holder such that the detector automatically rotates through twice the angle through which the holder is rotated. Thus the detector and the light source will be effectively equi-angularly located from a reference line perpendicular to the surface of the sample, that is, the detector will be located to detect a specularly reflected component of the light beam at an angle of reflection which is equal to the angle of incidence of the light beam on the sample surface.

For a better understanding of the invention and to show how the same may be carried into effect, embodiments thereof will now be described, by way of non-limiting example only, with reference to the accompanying drawings.

DETAILED DESCRIPTION OF EMBODIMENTS

Figure 1:
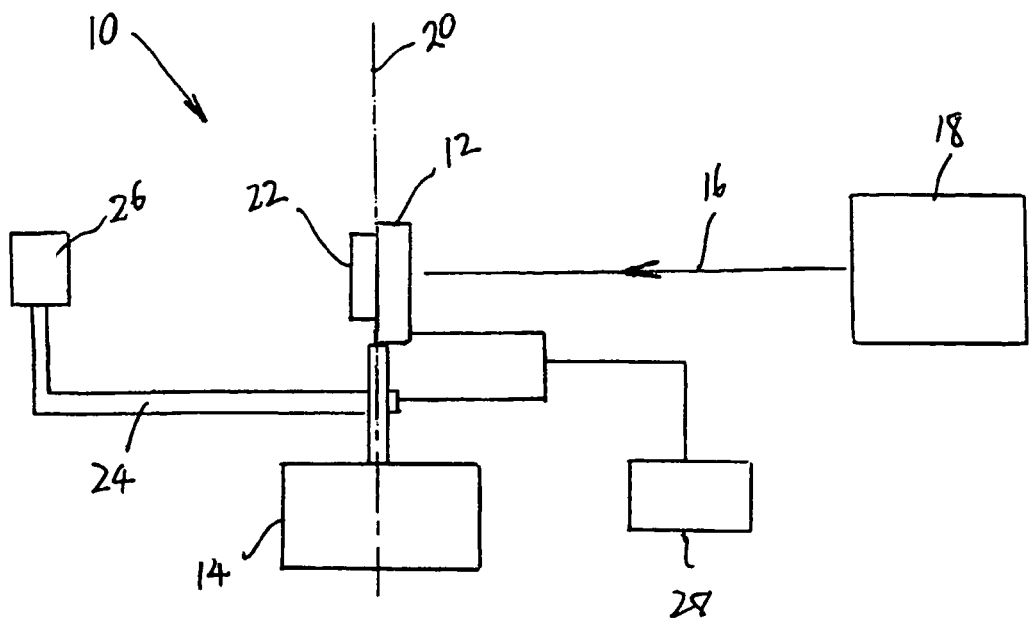
FIG. 1 schematically shows apparatus according to an embodiment of the invention.

Accessory apparatus 10 for measuring specular reflectance of a sample as illustrated in FIG. 1 includes a sample holder 12, which is mounted through bearings (not shown) onto a mount 14 so as to be automatically aligned with a light beam 16 which is transmittable from a light source 18 of a spectrometer. The bearings allow rotation of sample holder 12 with respect to mount 14 about an axis 20, but not lateral or vertical movement. Axis 20 passes through the point where light beam 16 strikes the surface of a sample 22 mounted in sample holder 12. An arm 24 is attached concentrically with sample holder 12 and carries at its outer extremity an optical detector 26. Arm 24 is mounted such that it is able to rotate around axis 20. A positive drive mechanism 28 (described in detail hereinbelow) is provided between arm 24 and sample holder 12 such that rotation of arm 24 also causes rotation of sample holder 12. The drive ratio of the drive mechanism 28 is such that when arm 24 is rotated through X degrees clockwise, the sample holder 12 rotates through X/2 degrees clockwise, and similarly for anti-clockwise rotation.

Figure 2:
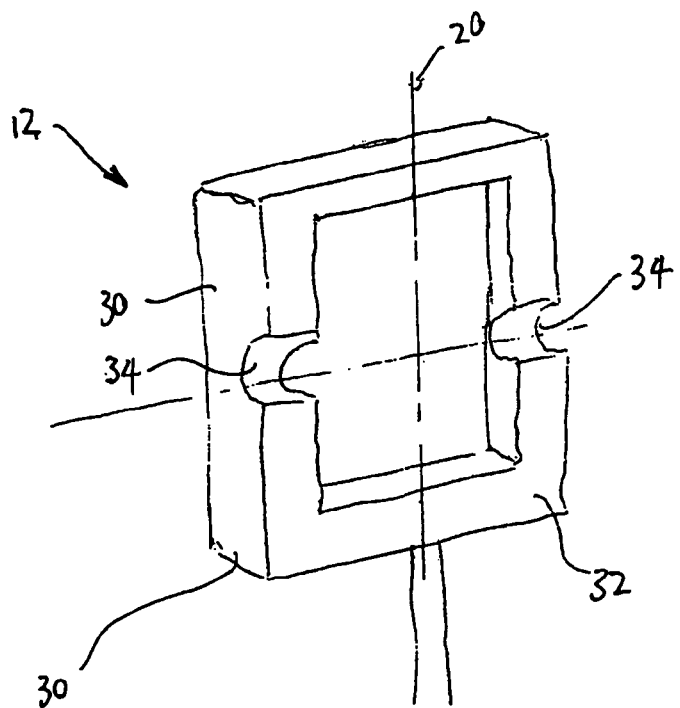
FIG. 2 schematically shows a sample holder of the FIG. 1 apparatus.
Figure 4:
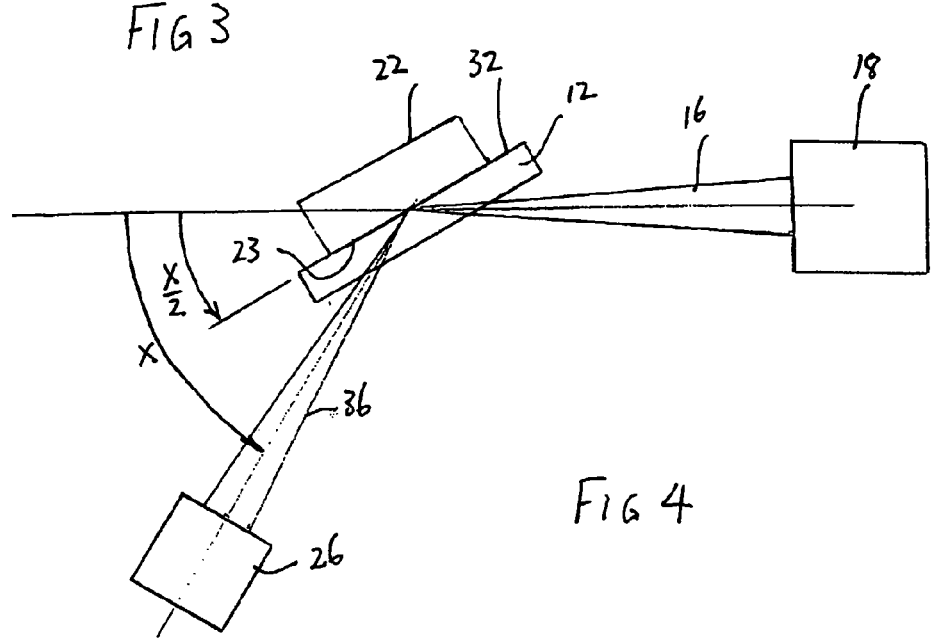
FIG. 4 schematically shows a top view of the apparatus of FIG. 1 with the components relatively positioned to make a sample measurement.

Sample holder 12 has the form of a frame 30 (see FIG. 2) which provides a mounting face 32 for correct alignment of a surface 23 (see FIG. 4) of sample 22 (the reflectivity of which is to be measured) in the apparatus 10. Thus sample 22 is mounted to sample holder 12 such that its surface 23 is held in facing contact with mounting face 32 of sample holder 12 by appropriate clamping means. Axis 20 coincides with surface 23 of sample 22 when the sample is mounted on the sample holder 12. The frame 30 of sample holder 12 includes cut-outs 34 for a purpose described below.

Figure 3:
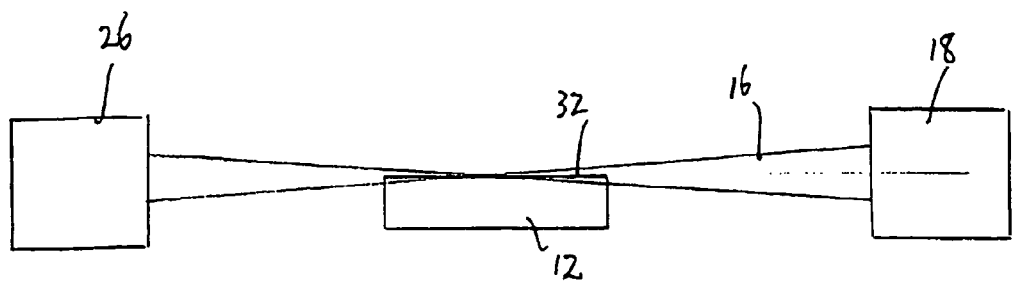
FIG. 3 schematically illustrates a top view of the apparatus of FIG. 1 with the components relatively positioned to make a reference measurement.

In operation, arm 24 is first rotated via drive mechanism 28 such that detector 26 directly intercepts light beam 16 with no sample present (see FIG. 3). It is essential that light beam 16 is not blocked by sample holder 12 with detector 26 in this position. This can be ensured by having sample holder 12 appropriately shaped to allow unobstructed passage of the light beam 16, that is, it may have the cut-outs 34 as described hereinabove. Alternatively, sample holder 12 can be made removable so that it can be temporarily removed from the apparatus. Detector 26 now measures the absolute intensity of light beam 16. This first measurement is a reference measurement. Arm 24 is then rotated via drive mechanism 28 to the desired measurement angle. If sample holder 12 has been removed it is replaced. Sample 22 is placed in sample holder 12 with its surface 23 in contact with face 32 of holder 12 (see FIG. 4). Light beam 16 now strikes surface 23 of sample 22 and the specularly reflected component 36 is intercepted by detector 26. Detector 26 records the intensity of the light reflected from surface 23 of sample 22, providing a second measurement. This second measurement is referred to as a sample measurement. The ratio of a sample measurement to the reference measurement gives the absolute reflectance of the sample at that angle. A number of sample measurements can be made at various angular settings of arm 24. A measure of the specular reflectance of sample 22 as a function of the angle of incidence of the light beam 16 can be determined in this way.

Figure 5:
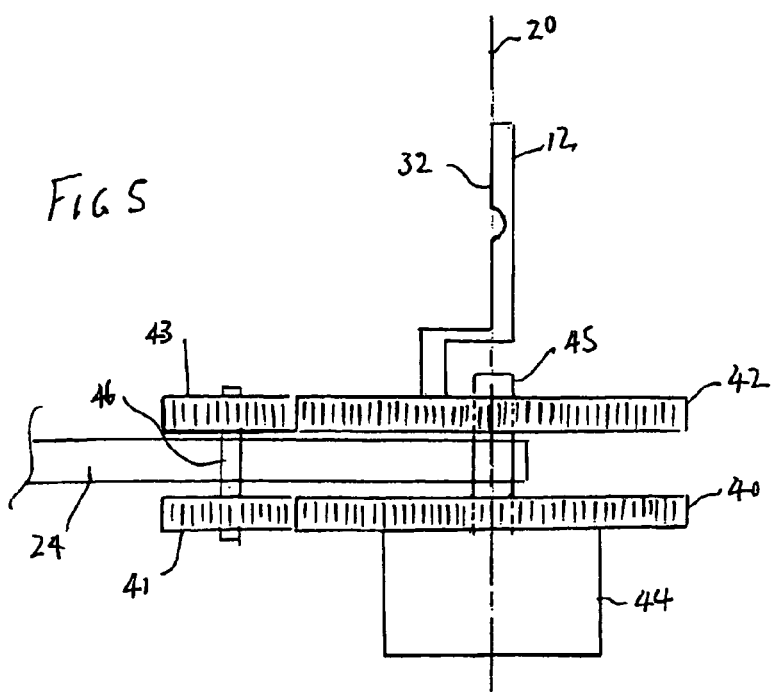
FIG. 5 schematically illustrates a drive mechanism for the apparatus of FIG. 1.

One arrangement for the drive mechanism 28 is shown in FIG. 5. It involves four gears 40, 41, 42 and 43. Gear 40 is attached to the body of a motor 44, and is fixed thereto to prevent movement or rotation of gear 40 relative to motor body 44. Motor body 44 in FIG. 5 is equivalent to mount 14 in FIG. 1. Gears 41 and 43 are locked together so they are constrained to rotate at the same angular rate and are mounted on a single spindle 46 that is attached to and free to rotate in rotatable arm 24. Gear 42 is attached to sample holder 12 so that rotation of gear 42 also causes rotation of sample holder 12. To ensure that sample holder 12 rotates at one half the angular rate of rotation of arm 24, the pitch circle diameters (PCD) of the gears are chosen as follows:

PCD gear 40+PCD gear 41=PCD gear 42+PCD gear 43

PCD gear 40/PCD gear 41=0.5* PCD gear 42/PCD gear 43.

A convenient extension is to make the rotation of arm 24 and sample holder 12 motorised so as to allow automatic angular positioning. Thus motor 44 may be electrically driven and, as indicated in FIG. 5, gear 40 is locked to electric motor body 44 so as to prevent rotation of gear 40 relative to motor body 44. Gear 42 and sample holder 12 are both locked to motor spindle 45 and thus rotate at the same rate as spindle 45. The rotatable arm 24 is mounted to motor spindle 45 via bearings (not shown) that allow rotation of arm 24 relative to motor spindle 45. It will be appreciated that this described arrangement will cause arm 24 to rotate through twice the angle of sample holder 12.

Figure 6:
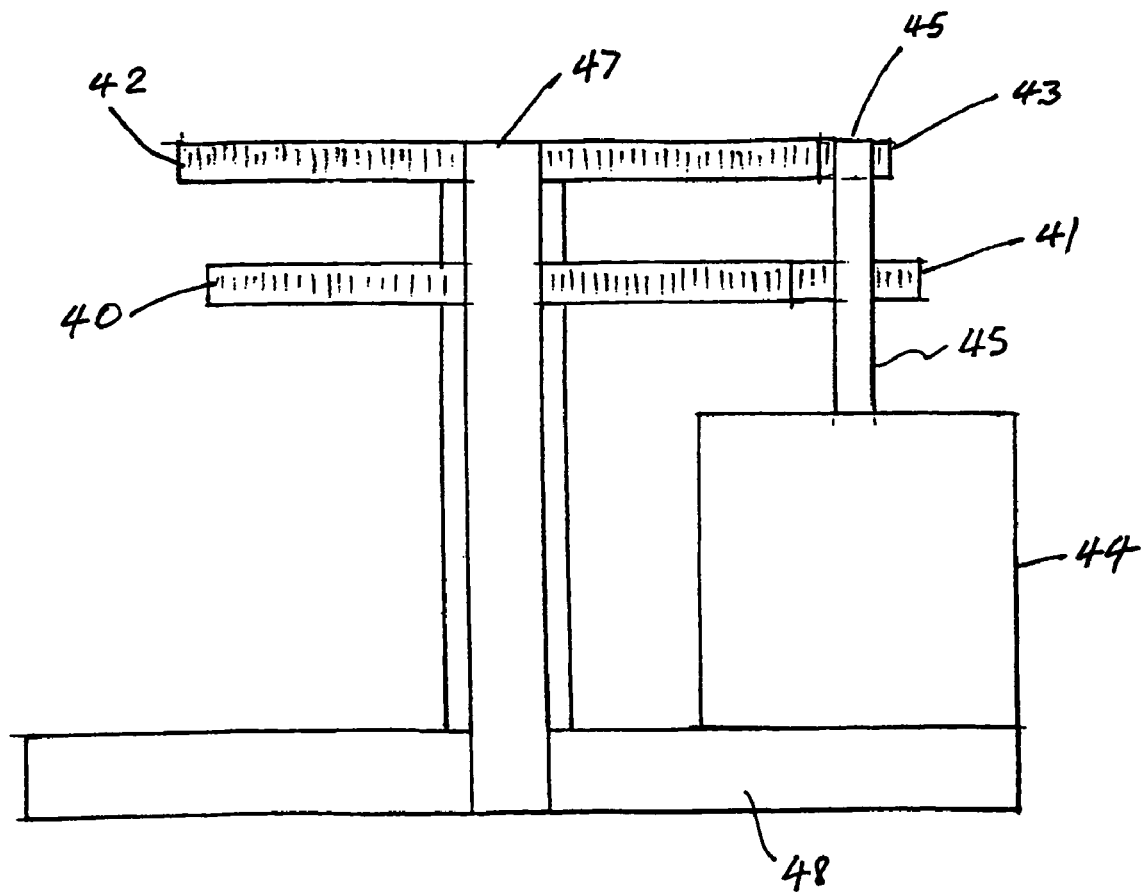
FIG. 6 schematically illustrates an alternative arrangement for the drive mechanism for the apparatus of FIG. 1.

FIG. 6 schematically illustrates another arrangement for the drive mechanism for the apparatus of FIG. 1 using similar gears 40, 41, 42, and 43. Gears 41 and 43 are fixed to the spindle 45 of motor 44. Gears 42 and 40 are free to rotate on a shaft 47. The sample holder (not shown) is fixed to gear 42, and the detector (not shown) is fixed to gear 40.

Rotation of the spindle 45 by motor 44 drives gear 40 at twice the rate of rotation of gear 42. The components are mounted on a base 48.

The above described apparatus besides being relatively simple, provides for the total path length from light source 18 to detector 26 to be the same for the first or reference measurement as it is for subsequent sample measurements at any angle. It also provides for the distance from light source to sample and sample to detector to be separately constant with changing angle of incidence. Consequently there is no change in optical focus point between reference and sample measurements. This eliminates the need for any optical re-imaging. Also the apparatus has the added advantages of requiring no mirrors and therefore its performance is not likely to deteriorate greatly with time. Those skilled in the art will appreciate that although there is no inherent need for optical re-imaging in the apparatus of the invention, there is also no requirement to exclude the use of optical re-imaging devices, or to exclude the use of a folding mirror or mirrors, provided always that all such devices or mirrors that are in the light path when the sample is in the light path must also be in the light path when the reference measurement is made without the sample in the light path, and provided also that all such devices or mirrors must always remain in a constant spatial relationship to the detector (i.e. they must move with the detector).

The invention described herein is susceptible to variations, modifications and/or additions other than those specifically described and it is to be understood that the invention includes all such variations, modifications and/or additions which fall within the scope of the following claims.

The invention claimed is:

1. Apparatus for measuring specular reflectance of a sample comprising:
    a sample holder,
    a light source for transmitting a beam of light at a predetermined angle of incidence onto a surface of a sample when held by the sample holder, the light source and the sample holder being mounted for relative movement to vary said angle of incidence; and
    a detector for detecting light of said beam which is specularly reflected from said surface of the sample, the detector and the sample holder also being mounted for relative movement,
    wherein the light source, the detector and the sample holder are correspondingly relatively positionable for a specularly reflected component of a transmitted light beam to be detected for different angles of incidence of the light beam and wherein corresponding relative positions of the light source, the sample surface and the detector are constrained such that said detector is located by said constraint to detect said specularly reflected component of said light beam at an angle of reflection, which is equal to the angle of incidence of the light beam on the sample surface, and wherein the detector for movement along an arc about said axis and the sample holder and the detector are operatively associated such that movement of the sample holder through an angle automatically rotates the detector through twice said angle.

2. Apparatus as claimed in claim 1, wherein the sample holder is structured, and the light source and the detector are positionable relative to the sample holder and each other, such that in the absence of a sample in the sample holder, the light source and the detector are positionable for a light beam transmitted from the light source to impinge directly on the detector.

3. Apparatus as claimed in claim 2, wherein the sample holder includes a frame that provides a mounting face against which the surface of the sample is locatable for correctly aligning the sample surface in the apparatus.

4. Apparatus as claimed in claim 3, wherein the frame is shaped to allow passage of a light beam transmitted from the light source to pass therethrough to impinge directly on the detector.

5. Apparatus as claimed in claim 1, wherein the sample holder is removably mounted such that in the absence of the sample holder the light source and the detector are positionable relative to each other for a light beam transmitted from the light source to impinge directly on the detector.

6. Apparatus as claimed in claim 5, wherein the sample holder, light source and detector are mounted such that the respective distances therebetween remain constant for different positionings of the sample holder, light source and detector, whereby the path length from the light source to the detector remains constant for reference and sample measurements at any angle.

7. Apparatus as claimed in claim 5, wherein one of the components of the group, the light source, sample holder and detector, is fixed in position and the other two components are moveable relative thereto.

8. Apparatus as claimed in claim 7, wherein the other two components are operatively associated such that movement of one correspondingly automatically moves the other to a correct position.

9. Apparatus as claimed in claim 7, wherein the light source is fixed in position and the sample holder and the detector are relatively moveable.

10. Apparatus as claimed in claim 9, wherein the sample holder is rotatable about an axis passing through the sample holder and perpendicular to the incident light beam such that the surface of a sample held by the sample holder is alignable at different angles to the direction of the incident light beam.

11. Apparatus as claimed in claim 9, wherein the detector is mounted on an arm which is rotatable about the axis about which the sample holder is also rotatable, and including a drive mechanism linking the arm and the sample holder for rotating the sample holder through an angle that is half an angle through which the arm is rotated.

12. Apparatus as claimed in claim 11, further comprising an electric motor for driving the drive mechanism wherein the drive mechanism comprises at least one gear train.

13. Accessory apparatus for a spectrometer for measuring specular reflectance of a sample comprising:
    a sample holder which is positionable relative to a light source of the spectrometer for the light source to transmit a beam of light at a predetermined angle of incidence onto a surface of a sample when held by the sample holder, the sample holder being mounted to be rotatable about an axis passing through the sample holder and perpendicular to the incident light beam from a light source of the spectrometer such that the surface of a sample held by the sample holder is alignable at different angles to the direction of the incident light beam, to vary said angle of incidence; and
    a detector for detecting light of said beam which is specularly reflected from said surface of the sample, the detector being mounted for movement relative to the sample holder along an arc about said axis, the sample holder and the detector are operatively associated such that movement of the sample holder through an angle automatically rotates the detector through twice said angle;

wherein the detector and the sample holder are correspondingly relatively positionable for a specularly reflected component of a transmitted light beam to be detected for different angles of incidence of the light beam.

14. Accessory apparatus as claimed in claim 13, wherein the sample holder is structured, and the detector is positionable relative to the sample holder and a light source of a spectrometer, such that in the absence of a sample in the sample holder, a light beam transmitted from the light source impinges directly on the detector.

15. Accessory apparatus as claimed in claim 14, wherein the sample holder includes a frame that provides a mounting face against which the surface of the sample is locatable, and the frame is shaped to allow passage of a light beam transmitted from the light source to pass therethrough to impinge directly on the detector.

16. Accessory apparatus as claimed in claim 13, wherein the sample holder is removably mounted such that in the absence of the sample holder the detector is positionable relative to the light source of a spectrometer for a light beam transmitted from the light source to impinge directly on the detector.

17. Accessory apparatus as claimed in claim 16, wherein the accessory apparatus is mountable relative to the light source and the sample holder and detector thereof are mounted such that the respective distances therebetween remain constant for different positionings of the sample holder and detector relative to the light source, whereby the path length from the light source to the detector remains constant for reference and sample measurements at any angle.

18. Accessory apparatus as claimed in claim 17, wherein the detector is mounted on an arm which is rotatable about the axis about which the sample holder is also rotatable, and including a drive mechanism linking the arm and the sample holder for rotating the sample holder through an angle that is half an angle through which the arm is rotated.

* * * * *